United States Patent [19]
Gratzl et al.

[11] Patent Number: 6,043,878
[45] Date of Patent: Mar. 28, 2000

[54] DEVICE FOR OPTICAL AND ELECTROCHEMICAL MEASUREMENTS IN MICROLITER SIZE SAMPLES

[75] Inventors: Miklos Gratzl; Andrea Cserey, both of Lakewood, Ohio; Kwong Yue Hui, Woburn, Mass.

[73] Assignee: Case Western Reserve University

[21] Appl. No.: 09/147,986

[22] PCT Filed: Sep. 24, 1997

[86] PCT No.: PCT/US97/17067

§ 371 Date: Jul. 9, 1999

§ 102(e) Date: Jul. 9, 1999

[87] PCT Pub. No.: WO98/13675

PCT Pub. Date: Apr. 2, 1998

Related U.S. Application Data

[60] Provisional application No. 60/026,605, Sep. 24, 1996, and provisional application No. 60/037,142, Feb. 14, 1997.

[51] Int. Cl.[7] ........................................................ G01N 1/10
[52] U.S. Cl. ............................................................. 356/246
[58] Field of Search .................................... 352/246, 244, 352/36, 38; 250/341, 343, 341.1

[56] References Cited

U.S. PATENT DOCUMENTS 5,658,723   8/1997   Oberhardt ................................. 435/4

*Primary Examiner*—Frank G. Font
*Assistant Examiner*—Michael P. Stafira
*Attorney, Agent, or Firm*—Fay, Sharpe, Fagan, Minnich & McKee

[57] ABSTRACT

A small liquid sample (24) to be tested is contained within an annulus (18) on the upper surface (14) of a substrate (12). In one embodiment, a reagent diffuses into the sample through a membrane (28) in a junction hole (26), the junction hole connecting upper (14) and lower (16) surfaces of the substrate. Optical measuring equipment (70, 72) detects a measurable change in an optical property of the sample. In an alternate embodiment, a flow of gas (30), directed at the small liquid sample (24), causes the sample to flow in a controlled manner over the surface of an electrode (20), disposed on the substrate surface (14). In another alternate embodiment, a special averaging electrode (20) is disposed in a non-homogeneous sample (24). Highly reproducible and accurate hydrodynamic electrochemical studies and analyses of microliter size samples are thus achievable, without the need for moving mechanical parts.

16 Claims, 8 Drawing Sheets

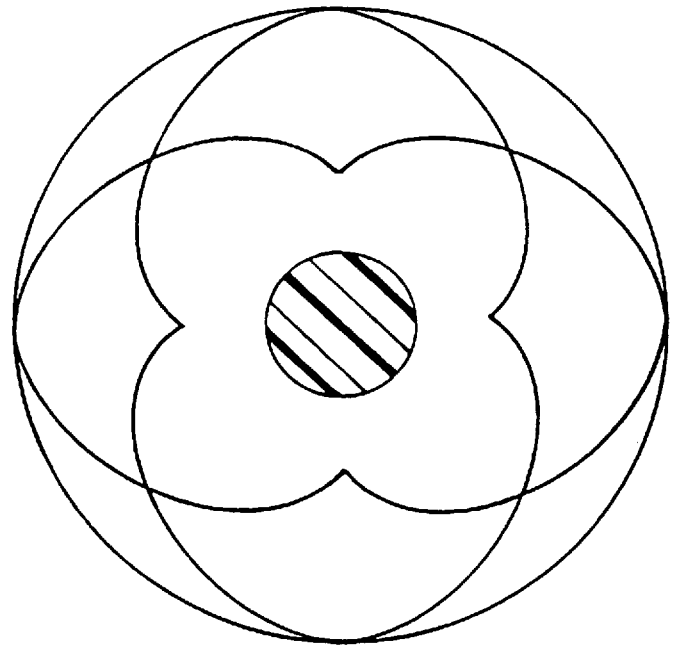
FIG. IIA
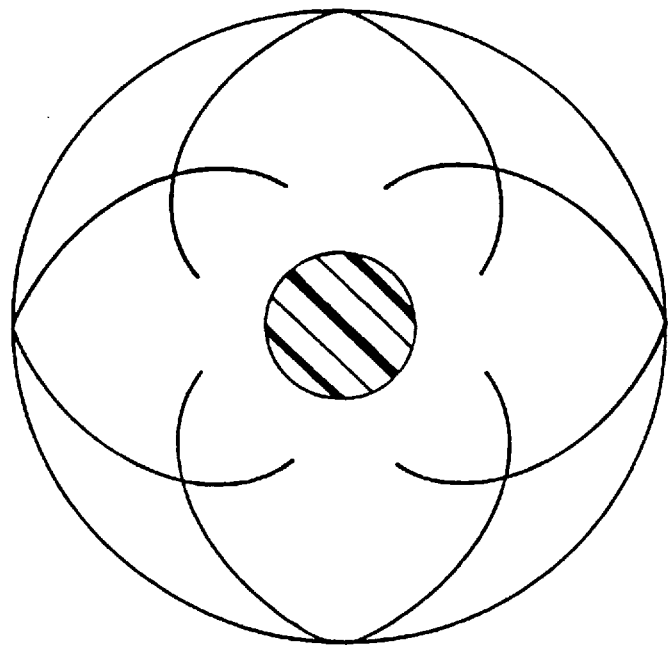
FIG. IIB

DEVICE FOR OPTICAL AND ELECTROCHEMICAL MEASUREMENTS IN MICROLITER SIZE SAMPLES

This application claims benefit of provisional application 60/026,605 Sep. 24, 1996, and 60/037,142, Feb. 14, 1997.

This invention was made with government support under Grant No. CA61860 awarded by the National Institutes of Health. The government has certain rights in this invention.

BACKGROUND OF THE INVENTION

The present invention relates to the analytical chemistry arts. It finds particular application in conjunction with the titrimetric analysis of microliter size samples. It also finds application in conjunction with instrumentation for electrochemical studies of microliter size samples and in studies where the rapid achievement of steady state conditions is desirable. Further, it finds application in conjunction with the electrochemical analysis of non-homogeneous samples. It is to be appreciated, however, that the invention is also applicable to other chemical procedures where precise microdelivery of a reagent is desirable.

I. Routine analysis of the chemical composition of fluids is important in a wide range of fields, including clinical diagnosis, food and drug industries, industrial process control, and environmental studies. Due to the accuracy and reliability that titrimetric methods provide, they are widely used in diagnostic tests.

For accurate results, however, laboratory expertise, relatively large sample volumes, and often devices with expensive micromechanical elements are required for titrimetric studies. In many areas, for example in forensic testing and clinical diagnosis, large quantities of a sample to be studied may be costly or not readily available. To maintain the accuracy of measurements as the size of the sample decreases, the cost of the titration equipment, and the level of skill required, generally increase. Automated addition of reagents further adds to the cost, particularly when delivering microliter size volumes or less.

II. Another analytical technique, the investigation of basic electrochemical reactions, is very important for industrial development in many fields, including semiconductors, the fuel industry, corrosion, quality control, and process monitoring. The rate of electrochemical reactions is limited by the rate of mass transport over the surface of the electrode.

However, the natural processes of diffusion can be accelerated by hydrodynamic electrochemical techniques.

Hydrodynamic electrochemical techniques with enhanced convective mass transport exhibit a number of advantageous voltammetric characteristics. The relative contribution of mass transport limitations with respect to electron kinetics is less pronounced. (Bard, A. J.; Faulkner, L. R.: *Electrochemical Methods*; John Wiley, (1980)). Steady state conditions (where the current is independent of potential scan direction and time) are attained quickly. Thus, measurements can be carried out with high precision. In addition, at steady state, double layer charging is not a factor.

Traditionally, one of the best methods of obtaining efficient convective mass transport uses a rotating electrode system, such as a rotating disc or ring-disc electrodes. In the latter case, the electrochemically generated species at the disc are swept by laminar flow past the ring, where they can be monitored. Both electrode types have proven to be useful in basic electrochemical studies, such as those of coupled homogeneous reactions (Kissinger, P. T. and Heineman, W. R., *Laboratory Techniques in Electroanalytical Chemistry*; Marcel Dekker (1984)) and short lived reaction intermediates (Zhao, M. and Scherson, D. A., 64 *Anal. Chem.* 3064–67 (1992)). Hydrodynamic methods also play an important role in electrochemical preconcentration techniques, such as stripping voltammetry or potentiometry, where enhanced mass transport allows for efficient extraction of the analyte on to the surface of the electrode. Preconcentration of heavy metal trace elements is particularly useful for the analysis of food, environmental, and biological samples, because of the large useful concentration range (1–10–2M), and the simpler, portable and less expensive instrumentation (Bersier, P. M., et al., 119 Analyst 2195–32 (1994)). Potentiometric stripping techniques have been used successfully in the determination of lead in blood samples (Jagner, D., et al., 6 *Electroanalysis* 285–91 (1994)), in gasoline (Jagner, D., et al., 267 *Anal. Chim. Acta.* 165–69 (1992)), and of heavy metals in tap water (Jagner, D., et al., 278 *Anal. Chim. Acta* 237–42 (1993)).

In potentiometric stripping analysis, an oxidizing agent, added to the sample, is used for the stripping of the deposited analyte from the electrode surface. In voltammetric stripping analysis, an anodic voltammetric scan is applied. Potentiometric stripping has advantages over voltammetric stripping in that it is unaffected by dissolved oxygen present in the sample, and does not require sophisticated anodic scanning instrumentation, since the potential is detected in time. (Jagner, D. et al. 278 *Anal. Chim. Acta* 237–42 (1993)). However, the potentiometric method has a number of disadvantages. For low sample concentrations, the fast stripping rate requires a very high real time data acquisition rate. Also, reproducible hydrodynamic conditions are more important than in anodic stripping, since the driving force of the oxidation is diffusion controlled mass transport.

The detection limit of hydrodynamic techniques can be further reduced by sinusoidally modulating the rotation speed of the electrode (Miller, B. and Bruckenstein, S., 46 *Anal. Chem.* 2026–33 (1974)).

III. Without techniques for rapid stirring of a test solution, electrochemical transducers, such as simple and modified electrodes, only provide information from the solution layer directly covering, and adjacent to, the sensing surface of the particular electrode used. While optical analytical techniques can produce chemical and other information that reflects bulk solution properties, rather than only surface characteristics, ordinary electrodes are interfacial devices, reflecting only surface characteristics, for example chemical composition at the electrode interface with the solution. Inhomogeneity occurs, for example, when a reagent is introduced to the sample in a nonuniform manner, such as through a membrane in the sample container.

As a consequence, when samples with inhomogeneities are to be analyzed for their average characteristics, electrochemical transducers generally are not suited to making such measurements, unless sufficient stirring of the solution is used to render the sample homogeneous.

For some applications, stirring of the solution is not practical, nor feasible.

IV. The principle of pH-statting (keeping the pH constant) of a sample where an enzyme reaction would otherwise cause the pH to steadily shift was first applied by Knaffl-Lenz in 1923, to establish the rate of an esterase reaction where the enzyme splits an ester into an alcohol and an acid. (Knaffl-Lenz—See Ref. 1) Thus, to keep the pH constant during this process, Knaffl-Lenz kept adding the required amount of base solution to the sample. The rate of addition which ensured an approximately constant pH was used to characterize the rate of the enzyme reaction, i.e. enzyme activity, in the particular experiment. Addition of the base was performed convectively (mechanically), by adding increments of the base solution using the feedback from the actually observed pH.

Today, the same principle is still used for enzyme activity measurements, except that the equipment involved has become more sophisticated. Fully mechanized and automatized instruments are now available that use a pH glass electrode or other method to monitor pH continuously. A feedback control loop (typically a PID controller) ensures that the right amount of acid or base is added at all times. Both analog and digital (computer based) controllers are available and reagent addition can occur in increments or even continuously.

A good description of such a state-of-the-art instrument and its performance and potential applications can be found in "Reaction Kinetics: pH-Stat Analysis with the TitriLab Titration System" (Application Notes, Radiometer—Copenhagen ©1996). Radiometer, Inc. is one of the leading manufacturers of such devices. The range of applications of the technique, however, has become much broader than the original aims of Knaffl-Lenz. The range encompasses determinations in the following areas: 1. Activity of enzymes. 2. Neutralization properties of drugs and other products (e.g. neutralization capacity, and reaction times of antacids). 3. Dissolution rates of minerals and additives for agricultural use (soil chemistry, animal feeds, etc.) 4. Acidity/alkalinity of samples. 5. Biological acid production (bacteria, cells, tissues, etc.). 6. Calcium build-up in muscles.

Many other applications exist or are evolving in research, industry, environmental management and medicine.

The instrumentation, due to the fact that is uses convective (mechanical) addition of an acid or base solution to the samples, requires sensitive and expensive mechanical parts whose fine regulation is complicated. Instruments are, therefore, expensive and require intensive maintenance. Reagent consumption is also high. The typical instrument consists of many different parts that all can malfunction (e.g. autoburette, driving motor and controller, reagent reservoirs, etc.). Another drawback is that relatively large samples are needed, otherwise the mechanical mode of reagent addition may not be fine enough to compensate for the tiny amounts of acid or base produced in a truly small (e.g. 1–20 microliter) sample.

There exists a need for a device for performing analyses on microliter size samples without the requirement for expensive microdelivery systems or extensive laboratory expertise.

Further, there exists a need for hydrodynamic techniques capable of being performed in microliter volumes. The existing techniques discussed all suffer in that they require sample volumes in the mL range. Constructing a rotating electrode of the smaller dimensions required for microliter sample volumes is not economically or mechanically feasible. Reproducibility of hydrodynamic conditions also becomes more difficult for smaller sample volumes.

Further, there exists a need for electrochemical techniques capable of analyzing a non-homogeneous sample and providing an average measurement corresponding to the solution as a whole, without mixing the sample.

Finally, there exists a need for pH-statting of microliter sized samples.

The present invention provides a new and improved apparatus and method for studies and analyses of microliter size samples which overcomes the above referenced problems and others.

SUMMARY OF THE INVENTION

In accordance with one aspect of the present invention, an apparatus for titrimetric analysis of microliter samples is provided. The apparatus includes a substrate, including an upper surface for supporting the sample to be investigated, and a lower surface. The apparatus also includes a container, sealed to the upper surface of the substrate, for containing the sample on the substrate. The apparatus is characterized by the container including an annulus that confines the sample on an area of the substrate upper surface bounded by the annulus, and by a junction hole, passing through the substrate and connecting the upper surface of the substrate with a lower surface of the substrate. A membrane covers the junction hole. The membrane permits diffusive movement of a reagent through the junction hole and into the sample. A source of reagent, disposed adjacent to the lower surface of the substrate, supplies reagent to the membrane. Analyzing equipment detect a measurable change in a property of the sample.

In accordance with another aspect of the present invention, a method of titrimetric analysis of microliter samples is provided. The method is characterized by disposing a sample to be tested in the apparatus described above. The sample is deposited on the upper surface of the substrate, in the area bounded by the annulus. A reagent is added to the droplet by diffusion of the reagent through the membrane. Measurements are made on the sample, the measurements corresponding to a chemical property of the sample.

In accordance with yet another aspect of the present invention, an apparatus for performing electrochemical studies and analyses on a small liquid sample is provided. A substrate includes an upper surface for supporting the sample to be investigated. An electrode is electrically connected to the sample. A container, sealed to the upper surface of the substrate, contains the sample on the substrate. The apparatus is characterized by the container including an annulus which confines the sample on an area of the substrate upper surface bounded by the annulus. A source of gas directs a flow of gas toward the sample, thereby causing controlled liquid flow over the electrode.

In accordance with yet another aspect of the present invention, a method of performing electrochemical studies and analyses is provided. The method is characterized by disposing a sample to be tested in the apparatus for performing electrochemical studies described above by depositing the sample on the upper surface of the substrate in the area bounded by the annulus. A flow of gas is directed onto the sample, thereby causing controlled liquid flow over the electrode. Electrochemical studies are conducted on the sample.

In accordance with another aspect of the invention, an apparatus for electrochemical analysis of a non-homogeneous sample is provided. An electrode is disposed in a solution of the sample to be analyzed. The method is characterized by the shape of the electrode and its disposition in the sample being selected such that an output of the electrode relates to a spatial average of a property of the sample.

In accordance with another aspect of the invention, an apparatus for pH-statting of a sample is provided.

The apparatus includes a working electrode disposed in the sample and a counter electrode. The working electrode applies a current to the sample to generate an ion in the sample. The ion is one of the group comprising hydrogen and hydroxyl ions. The counter electrode is separated from the sample by an electrochemical junction. The counter electrode generates a complementary ion that is separate from the sample so that the pH of the sample is not influenced by the complementary ion.

One advantage of the present invention is that it enables accurate titrations of microliter samples to be performed, without the need for expensive titration equipment.

Another advantage of the present invention is that delivery of reagents is achieved, without the requirement for moving mechanical parts.

Another advantage of the present invention is that controlled addition of reagents is readily obtained at very low addition rates.

Another advantage of the present invention is that reagents are added by diffusion, in concentrated form, so there is little change to the sample volume.

Another advantage of the present invention is that, by proper selection of the apparatus dimensions, the sample drop assumes a semispherical shape, such that it can be used as a lens to focus light passing through it on to an optical detector.

Another advantage of the present invention is that reproducible and rapid mixing of the sample is readily obtained.

Another advantage of the present invention is that there is no requirement for moving mechanical parts.

Another advantage of the present invention is that it enables simultaneous analysis and studies of several samples using the same mixing and stirring system and a single set of electrochemical instrumentation.

Another advantage of the present invention is that the geometries of the sample and electrochemical cell are reproducible due to the operation of surface tension and adhesion/repulsion forces.

Another advantage of the present invention is that connections to the working electrode are simplified since the electrode is stationary.

Another advantage of the present application is that it enables electrochemical measurements corresponding to an average property or properties of a non-homogeneous solution to be made without the need for stirring of the solution.

BRIEF DESCRIPTION OF THE DRAWINGS

The invention will take form in various components and arrangements of components, and in various steps and arrangements of steps. The drawings are only for the purposes of illustrating a preferred embodiment and are not to be construed as limiting the invention.

FIGS. 11(A)–11(B) is a comparison of exact and approximate solutions for a "flower" sensor, derived from equations 5 and 6 respectively, in accordance with the present invention.

DETAILED DESCRIPTION OF THE PREFERRED EMBODIMENTS

The embodiments described all make use of an arrangement suited to investigation of microliter sized samples which includes the disposing of a small sample droplet within an annular ring on a substrate support. The apparatus is modified according to the nature of the investigation, for example, by the incorporation of electrochemical and optical methods for following the progress of a reaction within the sample. Techniques such as stirring of the sample by a flow of gas, or introduction of reagents through a junction hole in the substrate, optionally supplement these analytical methods. As will be described for each of the embodiments, however, the applications are generally suited to macroscopic as well as microscopic studies.

I. Optical Measurements

Figure 1:
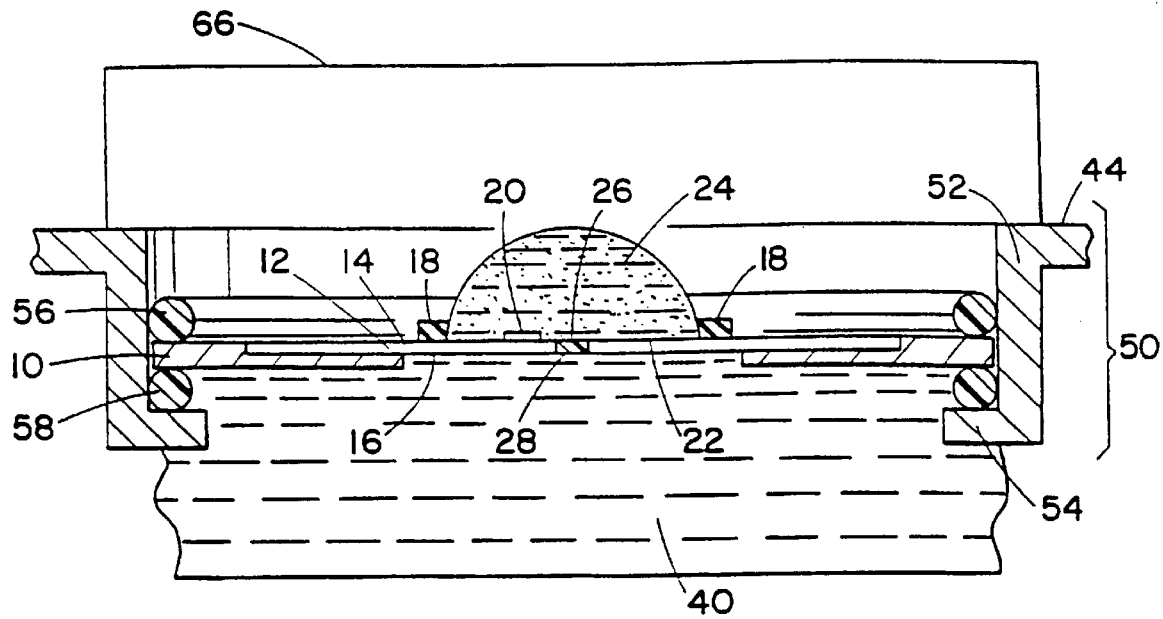
FIG. 1 is a schematic diagram of a top view of a sample holder for an apparatus for performing measurements on a small liquid sample in accordance with the present invention.
Figure 2:
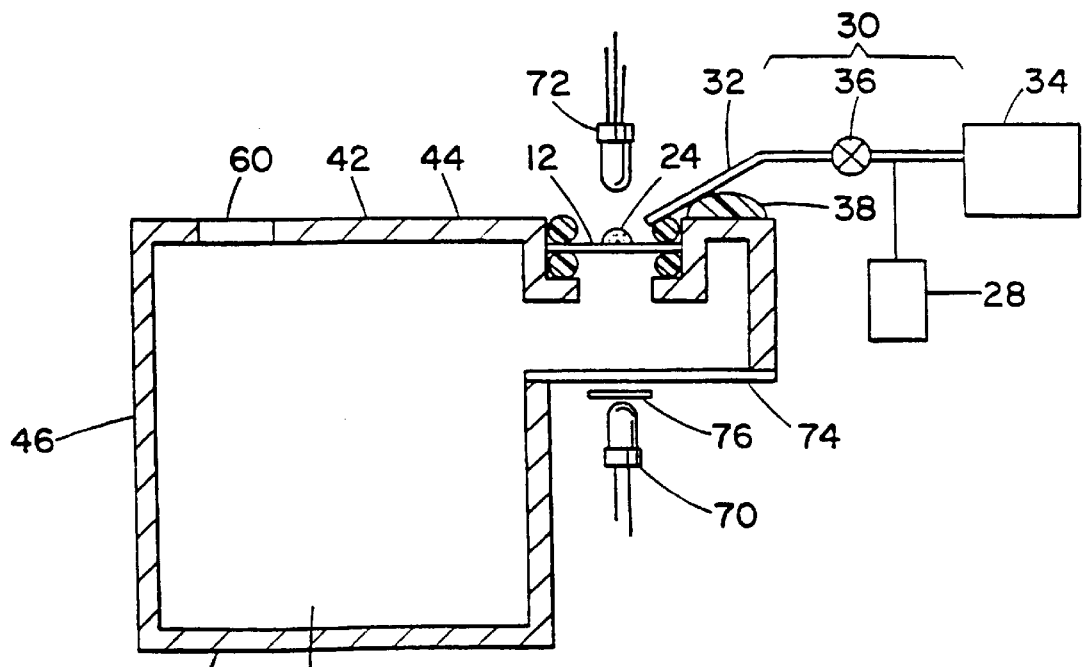
FIG. 2 is a schematic diagram of a side view of the apparatus of FIG. 1 in accordance with the present invention.
Figure 3:
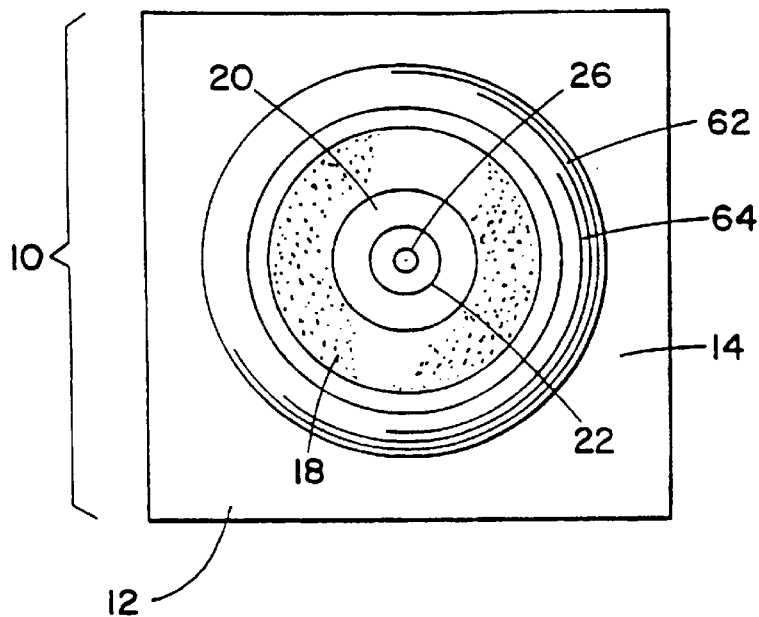
FIG. 3 is a schematic diagram of a sample holder and sample support for the apparatus of FIG. 1 in accordance with the present invention.

With reference to FIGS. 1 and 2, and 3, a sample holder 10 includes a substrate or plate 12, including upper and lower surfaces 14 and 16 respectively, and a sample container or hydrophobic ring 18, affixed to the surface of the substrate 14. A sample droplet 24 of the substance to be studied is applied to an area 22 of the substrate surface 14 bounded by the hydrophobic ring 18. The drop is centered automatically by the hydrophobic ring 18 and natural surface tension and adhesion/repulsion forces. A junction hole 26 connects upper and lower substrate surfaces 14 and 16. A membrane or gel 28 seals the junction hole 26. The membrane 28, permits diffusion of a reagent 40, from a reagent container or source 42, disposed adjacent the lower surface of the substrate, into the sample droplet 24. Optionally, a mixing system 30, mixes the droplet to enhance the rate of mixing via diffusion.

The substrate 12 is constructed from a material such as Pyrex®, which is unreactive towards the chemicals under investigation. Surface 14 is preferably flat, but may optionally be indented to hold the sample droplet.

The sample container 18 is constructed of a material that is unreactive toward the chemicals under investigation and which maintains the droplet in a bounded area on the surface 14 of the substrate. Where the droplet is primarily hydrophilic, such as water, the sample container 18 preferably includes a hydrophobic ring, such as an annulus of silicone elastomer. For hydrophobic organic samples, a hydrophilic ring is preferred. For sample droplets of approximately 20 μL, an annulus 18 with an inner diameter of 4.2 mm ensures that each droplet assumes a semispherical shape. The small junction hole 26 is preferably located in the center of area 22, joining surfaces 14 and 16 of the substrate 12. The membrane or gel 28 sealing the junction hole 28 is optionally a low melting point agar gel (3%), and serves as a diffusion path for the reagent 40, between the reagent source 42 and the sample droplet 24. Reagent delivery via diffusion is intrinsically automatic and does not require moving mechanical parts. The choice of the membrane or gel material and its thickness, and the diameter of the junction hole 26, influence the rate of reagent diffusion into the sample droplet 24.

Although the junction hole 26 is an effective means for delivering the reagent 40 to the sample 24, other arrangements whereby the reagent diffuses through a membrane 28 into the sample are also contemplated. For example, the membrane could be located in a wall of the sample container 18, or in a bridge, connecting the source of reagent 42 with the sample.

When the mixing system 30 is employed, the diffusive delivery rate of the reagent 40 is enhanced by placing the junction hole 26 off center, to make use of the higher flow rates there. optionally the gel 28 is a voltage sensitive gel. This allows direct control of the diffusional delivery of the reagent 40 through the gel 28.

The reagent container 42 optionally includes a top 44, side 46, and a base wall 48, respectively, the top and base walls being sealed to the side wall. A reagent inlet 60 is disposed in the top wall 44 of the reagent container, through which the supply of reagent 40 is replenished.

The reagent container 42 preferably includes a sample holder support 50 for holding the sample holder such that reagent 40 is in contact with the gel 28 at the lower surface 14 of the substrate. The sample holder support 50 optionally includes a support tube 52, depending downwards from the top of the reagent container 44 into the reagent 40. The tube 52, has approximately the same internal cross sectional dimensions as that of the sample holder 10 such that the sample holder slides down the tube. A lip 54, extending inward from the tube 52, at a distance from the top of the reagent container 44, holds the sample holder 10 in a horizontal position within the tube. Upper and lower O-rings 56 and 58, respectively, seal the sample holder in the tube 52 and prevent loss of reagent 40 through the tube.

The apparatus is suited to a variety of analytical techniques, including electrochemical monitoring, phosphorescent, or fluorimetric analysis, and optical measurement. The apparatus is particularly suited to optical measurement as the sample can be forced to assume a semispherical shape by using surface tension and capillary forces and proper special constraints. The sample droplet 24 can thus be used as a lens, helping to focus light passing through it. There is little change in the size of the droplet 24, during reagent addition, as the reagent 40, enters the droplet in concentrated form through diffusion through the gel 28. Thus, where continuous addition of a chemical is accompanied by some type of optical change, a simple optical measuring system serves to indicate the progress of the chemical reaction taking place in the sample drop 24. These optical changes may be inherent to the chemistry of the reaction taking place, or may be artificially induced by the addition of a selected optical dye or indicator to either the sample 24 or to the reagent 40, or both, before the diffusional delivery of the reagent and optical measurements are begun.

For optical measurements, a light source 70, such as a low cost, low power LED, preferably directs light at the droplet 24. Light emitted from the droplet 24 is detected by a receiver 72, such as a phototransistor detector. A change in an optical property of the sample droplet 24, such as a color change, results in a measurable change in the transmitted light detected by the receiver 72. For example, a titrimetric analysis accompanied by an abrupt color change at the end point will produce a curve with a corresponding sharp end point, which is facile to detect by analysis of the transmitted light detected by the receiver 72.

Figure 4:
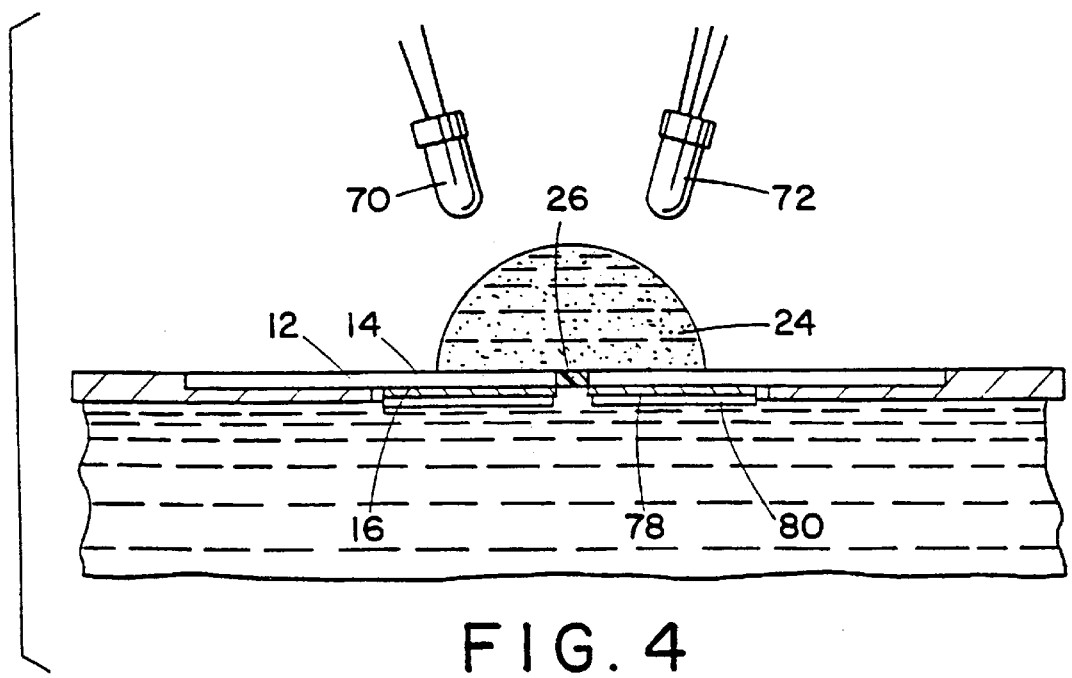
FIG. 4 is a schematic diagram of an alternative embodiment of an apparatus for performing measurements on a small liquid sample in accordance with the present invention.

With reference to FIG. 3, for reagents capable of transmitting light from the light source 70, the reagent container 42 preferably includes a window 74, that transmits light from the light source 70. Sample holder is also optically transparent to at least a selected wavelength of light. Light thus passes from the source 70 and through the reagent 40 and the sample holder 10 to the sample droplet 24. Preferably the walls of the reagent container 42, apart from the window 74, are constructed of an opaque material, such as dark plexiglass, that limits transmission of light in the wavelengths under investigation.

Where the reagent 40 is highly colored or turbid, such that light does not easily pass through the reagent, FIG. 4 shows an alternative arrangement. A highly reflective substance 78, such as chromium, coats the lower side 16 of the substrate 12. A layer of an inert substance 80, such as epoxy, is optionally deposited over the reflective substance 78 to protect it from damage or corrosion by the reagent 40. Light source 70 and receiver 72 are located on the same side of the droplet, above the upper surface 14 of the substrate 12. Light from the source 70 passes through the droplet 24 and is reflected back through the droplet by the reflective substance 78.

Optionally, light filters 76, such as gelatin or plastic filters, applied to the light source 70, the detector 72, the sample holder 10, or a combination of these, limit the wavelengths of light received by the receiver 72. This reduces extraneous noise in the signal. Alternatively, transmittance at two or more wavelengths is detected simultaneously by using a wide wavelength or dual source 70 and dual receivers or spectral receiver 72. This is particularly suited to dyes where the ratio of transmittance at two selected wavelengths is proportional to the analyte concentration in the sample droplet 24, over a certain range, and where there is no detectable abrupt end point. The system is also suited to continuous process monitoring, providing continuous, direct, rather than point, information.

With reference to FIG. 2, the mixing system, 30 optionally includes a gas supply tube 32, connected to a gas supply 34. The gas supply tube 32 directs a flow of gas tangentially at the sample droplet 24, for mixing of the sample. The gas supplied through supply tube 32 is preferably an inert gas, such as nitrogen. The flow rate of the gas is controlled by a flow meter 36, connected between the supply tube 30 and the gas supply 34. The gas supply is preferably a cylinder of gas. Supply tube 32 is constructed of an inert material such as Teflon, and ideally has an internal diameter of approximately 0.5 mm when the sample volume is around 20 μL. Optionally, a piece of adhesive material 38, such as tacky wax, holds the tube 30 in a fixed position. gas rapidly mixes the sample 24 with the incoming reagent 40, to create a homogeneous mixture. The rate of mixing is variable, dependent on the flow rate of the gas and the geometry of the tube 32, as well as on other factors, such as the size of the droplet 24. The geometry of the sample 24 is strictly reproducible due to surface tension and adhesion and repulsion forces which are strong for microliter size samples in the invented arrangements. Therefore the mixing system 30 mixes and stirs the sample droplet 24 in a reproducible manner. Thus, accuracy of analysis is improved.

For titration analyses on very small sample drops 24, such as those of around 1 microliter in volume, diffusion alone may be sufficient to achieve pseudoinstantaneous mixing of the sample drop and the reagent being delivered by diffusion into it. In such cases, the mixing system 30 is not required.

Optionally, a humidifier 28, connected to the mixing system 30 between the flow meter 36, and the gas supply tube 32, humidifies the gas directed at the sample 24. This reduces the tendency of chemicals in the sample droplet 24 to concentrate, through evaporation of water from the sample surface. Because of the large surface to volume ratio of the small droplet 24, evaporation occurs fairly rapidly in the absence of humidification. For titration experiments involving a distinct color change endpoint, however, evaporation is not material.

Additionally, a well 62, formed by indenting the substrate 12 and filled with a fluid 64, such as distilled water, surrounds the hydrophobic ring 18 and humidifies the atmosphere around the droplet 24. Optionally, a buffer is added to the well 62 for maintaining the pH of the sample droplet 24. Calcium hydroxide, for example, added to the distilled water, prevents carbon dioxide in the air from affecting the pH of the sample droplet 24, and reduces evaporation. Additionally, a cover 66 surrounds the droplet 24, maintaining the atmosphere around the droplet and further reducing evaporation.

Although mixing by means of a gas flow is an effective method of enhancing the natural processes of diffusion within the sample 24, other mixing mechanisms are also envisaged. FIG. 3, for example, shows an alternative mixing system 30, including MEM micromotors 20, fabricated into the sample holder 10 for mixing the sample droplet 24.

II. Hydrodynamic Electrochemical Measurements

With reference to FIGS. 5–8, an apparatus more suited to hydrodynamic electrochemical measurements is shown. The apparatus optionally includes features of the apparatus described above for optical measurements. Like components are numbered accordingly.

A sample holder 10 includes a substrate or plate 12, including upper and lower surfaces 14 and 16 respectively, and a sample container or hydrophobic ring 18, affixed to the surface of the substrate 14. A working electrode 20, is preferably connected to the surface 14 of the substrate, centered within an area 22, bounded by the hydrophobic ring 18. A sample droplet 24 of the substance to be studied is applied to area 22 of the substrate surface 14 and centered automatically by the hydrophobic ring 18 and natural surface tension and adhesion/repulsion forces. A jet system 30, including a tube 32, connected to a gas supply 34 directs a flow of gas tangentially at the sample droplet 24.

The substrate 12 is constructed from a material such as Pyrex®, which is both unreactive towards the chemicals under investigation and an electrical insulator. Surface 14 is preferably flat, but may optionally be indented to hold the sample droplet. The thickness of the substrate 12 is preferably of the order of 0.25 mm.

Figure 5:
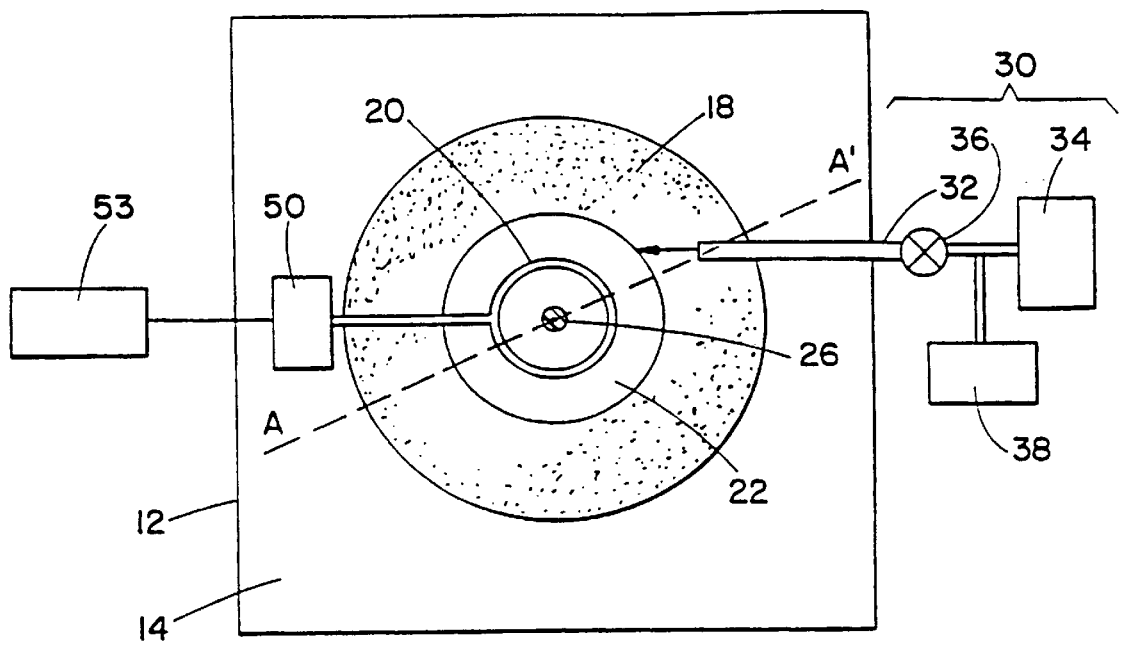
FIG. 5 is a schematic diagram of the top view of an apparatus for hydrodynamic electrochemical studies in accordance with the present invention.
Figure 6:
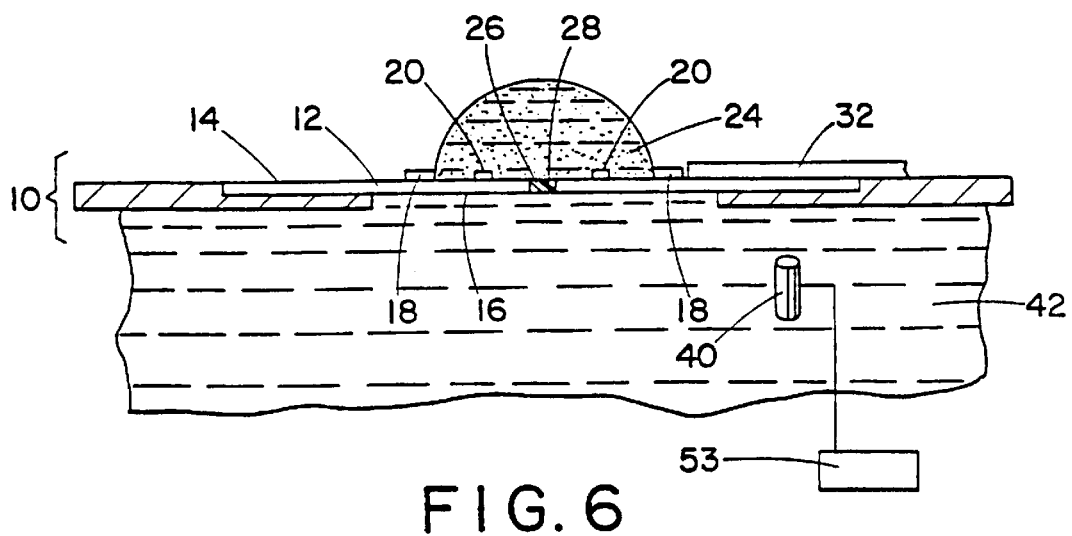
FIG. 6 is a schematic diagram of a side view though A–A' of FIG. 5 of an apparatus for hydrodynamic electrochemical studies in accordance with the present invention.

The electrode 20 shown in FIG. 5 is preferably a gold ring working electrode. For sample droplets of 20 $\mu$L volume, the electrode is preferably microfabricated by thin-film sputtering a ring of approximate dimensions 2.2 mm diameter, 0.2 mm width, and 5000 Å thickness onto the area 22 of the surface of the substrate 14. Because of the large electrode surface area to droplet volume ratio, exhaustive electrolysis of the electroactive species in the sample droplet occurs rapidly. The system is thus ideally suited to electrochemical preconcentration techniques, such as voltammetric and potentiometric stripping analyses.

The electrode is electrically connected to a contact pad 50, through which electrical measurements are made or voltages and currents applied. Preferably, the pad 50 is connected to automated electrochemical instrumentation 52.

The invention, however, is not limited to microfabrication techniques or electrodes 20 deposited on the substrate 12. Alternatively, conventional macro- and microelectrodes, alone or together with microfabricated ones, are used for studies and analyses of the sample droplets 24.

Optionally, a reference and/or counter electrode 40 immersed in an electrolyte solution 42 is in electrical contact with the sample 24. A silver/silver chloride electrode 40 in a saturated potassium chloride electrolyte 42 provides a good reference electrode. For cyclic voltammetry and constant potential electrolysis, a platinum spiral auxiliary electrode is desirable. Optionally, the electrode 40 is connected to electrochemical instrumentation 52.

Junction hole 26 preferably serves as a junction between the sample droplet 24 and the reference/counter electrode 40 and electrolyte 42. Alternatively, the reference or counter electrode 40 is connected to the sample droplet 24 by a traditional salt bridge arrangement.

The gas supplied through tube 32 is preferably an inert gas, such as nitrogen. The flow rate of the gas is controlled by a flow meter 36, connected between the tube 30 and the gas supply 34. The gas supply 34 is preferably a cylinder of gas. Enhanced mass transport to and from the electrode 20 is realized by the stirring effect of the jet system 30, which rotates the droplet 24 at a high rate. The rotation rate is variable, dependent on the flow rate of the gas and the geometry of the tube 32, as well as on other factors, such as the size of the droplet 24. Rotating and stirring the sample in this way also makes the connections to the electrode 20 much simpler since the electrode 20 is kept stationary, rather than rotating, as in a rotating disc electrode. In addition, performance of hydrodynamic electrochemical studies in small volumes, without the requirement for moving mechanical parts, can be achieved.

The geometry of the sample 24 is strictly reproducible due to surface tension and adhesion and repulsion forces which are strong for microliter size samples in the invented arrangements. Therefore the gas jet 30 mixes and stirs the sample droplet 24 in a reproducible manner. Thus, accuracy of electrochemical studies, such as potentiometric stripping, is improved.

Optionally the rotation rate of the sample droplet 24 is modulated by raising or lowering the gas flow rate, or the geometry of the tube 32, over time.

Results of cyclic voltammetry and constant potential electrolysis experiments carried out in 20 $\mu$L samples of potassium ferricyanide demonstrate that stirring of a semispherical microsample placed above a stationary ring electrode with a gas jet can be as effective as a rotating electrode system. The thickness of the diffusion layer at the surface of the stationary electrode 20, determined from the steady state plateau current, was as thin as at a conventional rotating electrode, i.e., of the order of 10 $\mu$m. Even thinner diffusion layers may be achieved by depositing the working electrode 20 further away from the center of area 22, or by using a somewhat larger sample droplet 24. (e.g. 50 μL.)

At very high gas flow rates (around 109 mL/min for the dimensions suggested above), there is a tendency for the sample droplet 24 to vibrate erratically, thus limiting the maximum rate of mass transport achievable within the droplet while maintaining steady state conditions. Flow rates of 101 mL/min or below eliminate these vibrational effects. Alternatively, the use of more than one tube 32 applying gas to the droplet 24, tends to reduce this tendency to vibrate and also allows different stirring patterns to be achieved.

The ratio of the surface area of the electrode 20 to the volume of the sample 24 is large in the arrangement shown in FIG. 5. Thus, exhaustive electrolysis of the electroactive species in the entire sample droplet 24 is achieved rapidly. The apparatus therefore, provides a simple, inexpensive, reproducible, and optionally disposable, means of electrochemical preconcentration, such as for voltammetric stripping analysis.

Optionally, reagents are added to the sample droplet 24 by controlled diffusion through gel 28. Reagents include oxidizing agents used in the case of potentiometric stripping analysis. Extremely low delivery rates are achievable in this way. In addition, the beginning of delivery can be timed at any point in the analysis. When required, the diffusive delivery rate of the reagent is enhanced by placing the junction hole 26 off center, to make use of the higher flow rates there.

Figure 7:
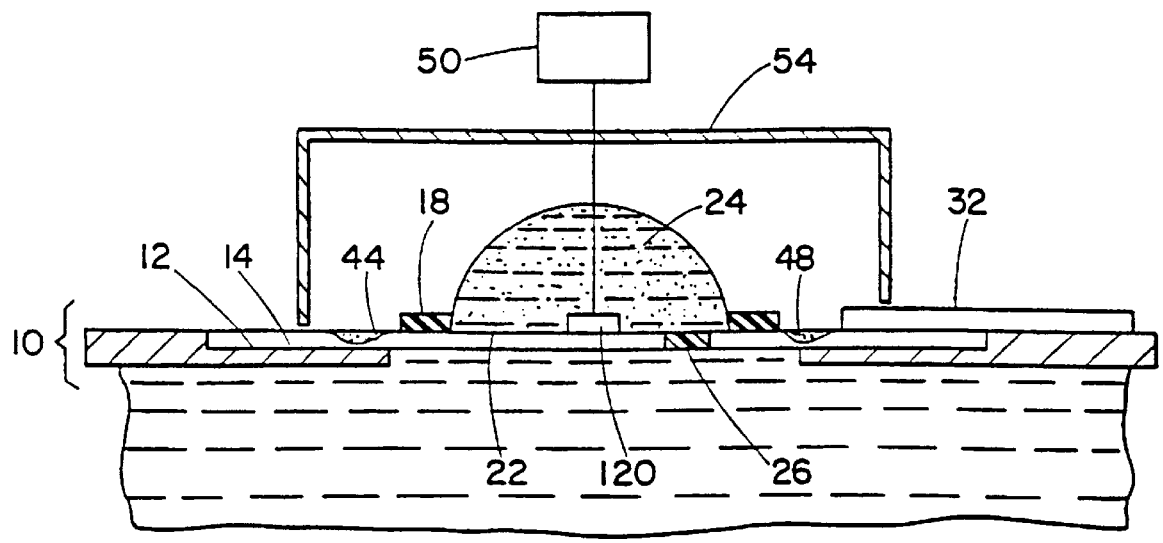
FIG. 7 is a schematic diagram of a side view of an alternative apparatus for hydrodynamic studies in accordance with the present invention.

Referring to FIG. 7, an electrode 120 with a small surface area, such as a dot electrode is situated in area 22. By reducing the area of the electrode to a dot, as opposed to the ring electrode 20 shown in FIG. 5, electrolytic exhaustion is effectively negligible. Thus the sample droplet 24 becomes stationary in terms of chemical composition, allowing for voltammetric studies that require longer times, such as kinetic studies or other electrochemical experiments that would normally require a rotating electrode system.

In such experiments, evaporation of the sample droplet 24 is prevented by humidifying the gas flow. Additionally, a well 44, formed by indenting the substrate 12, and filled with a fluid 48, such as distilled water, surrounds the hydrophobic ring 18 and humidifies the atmosphere around the droplet 24. Optionally, a buffer is added to the well 44 for maintaining the pH of the sample droplet 24. Calcium hydroxide, for example, added to the distilled water, prevents carbon dioxide in the air from affecting the pH of the sample droplet 24, and reduces evaporation. Additionally, a cover 54 surrounds the droplet 24, maintaining the atmosphere around the droplet and further reducing evaporation.

Figure 8:
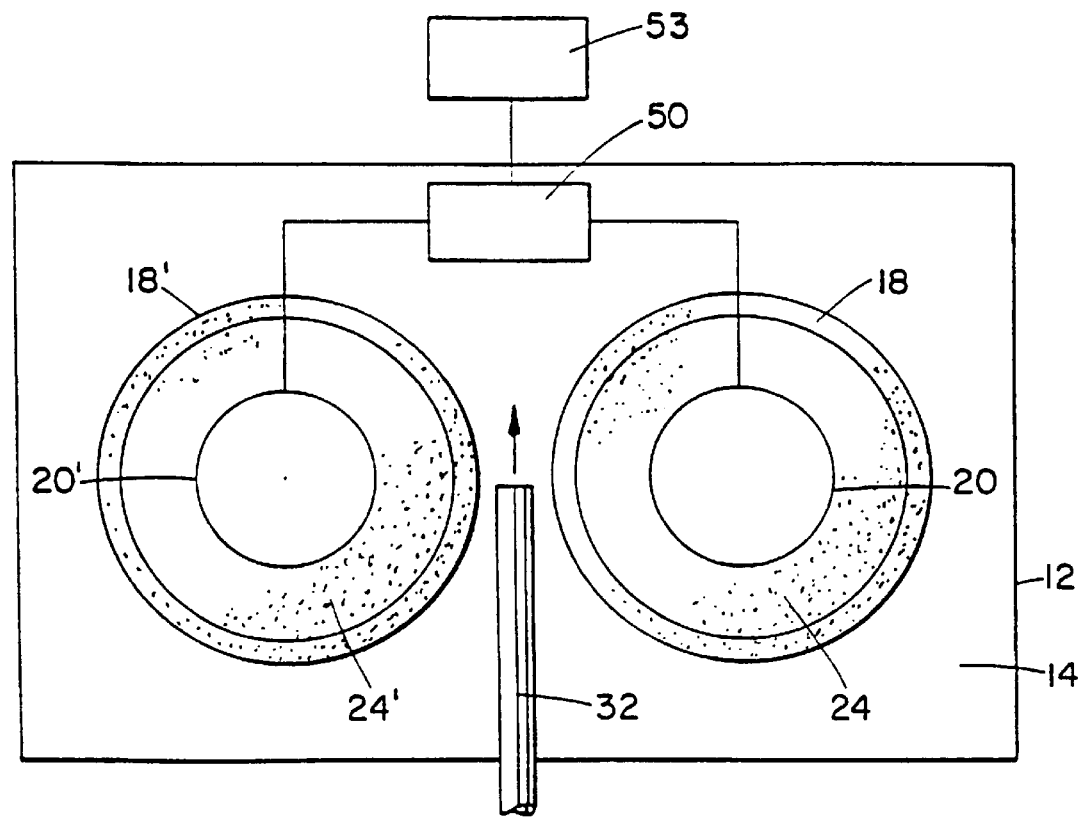
FIG. 8 is a schematic diagram of the top view of another alternative apparatus for hydrodynamic electrochemical studies in accordance with the present invention.

Referring to FIG. 8, simultaneous study of multiple samples is readily achieved. The jet system 30 is suited to stirring a number of sample droplets simultaneously. Optionally, sample droplets 24 and 24' are arranged in parallel, with a single tube, 32, providing the gas to stir both droplets. Thus, stirring is more uniform and sample droplets 24 and 24' are rotated laminarly. In addition, evaporation is reduced. The sandwich type arrangement shown in FIG. 8 is suited both to studies and analyses based on electrochemical preconcentration and also to kinetic studies, depending on the ratio of the electrode surface to the sample volume.

Alternatively, multiple tubes 32, multiplexed to the jet system 30, with each one directed to a separate sample drop 24 are employed. A single automated electrochemical monitoring apparatus 152, connected to each of the contact pads 50 allows selective sampling and monitoring of the reaction of each droplet 24.

III. Electrochemical Measurements on Non-Homogeneous Samples

Figure 9:
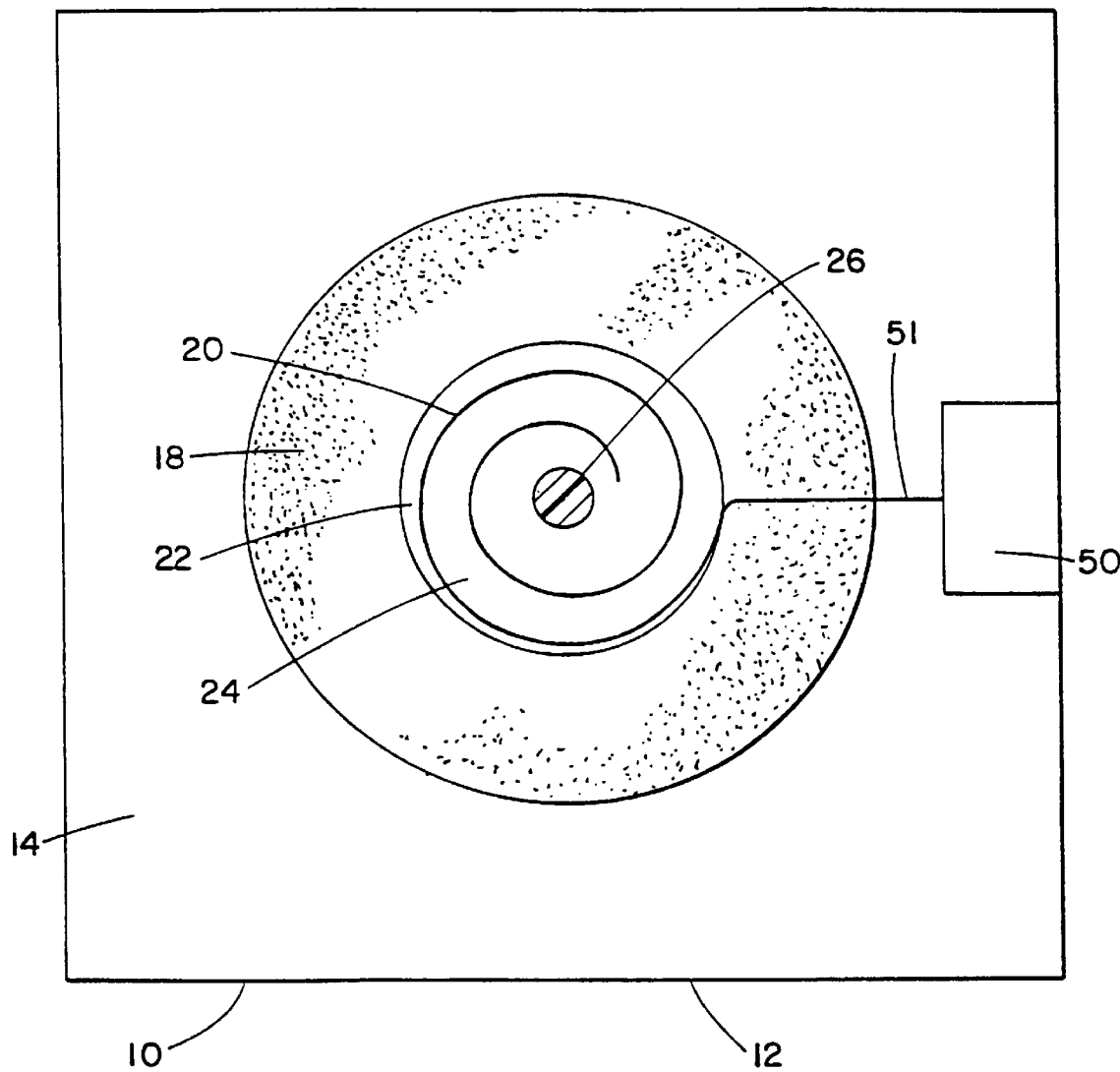
FIG. 9 is a schematic diagram of a top view of an apparatus for electrochemical analysis of a nonhomogeneous sample in accordance with the present invention.

With reference to FIGS. 9–10 apparatus particularly suited to the analysis of non-homogeneous samples is shown. Some of the electrodes described are suited to microfabrication procedures and to incorporation into the apparatus described above for analysis of microliter size samples. However, it should be appreciated that the electrode designs are also suited to analysis of larger samples, contained in conventional analysis receptacles known in the art.

It possible to design electrodes (i.e. simple as well as modified electrochemical transducers) that can obtain information on spatial average composition from inhomogeneous samples if the inhomogeneities exhibit certain spatial symmetries or spatial degeneration. These devices can be appropriately called spatially averaging electrochemical sensors, which can be used when stirring of the sample is not practical or not feasible, and an electrochemical transduction scheme needs to be used.

Design of such sensors only requires finding a suitable spatial layout of the sensor (i.e. shape and position with respect to the sample) to make sure that sensor output reflect concentrations that correspond (exactly, or approximately) to the actual spatial average concentration of the sample. Thus, to achieve this goal, well defined sensor and sample geometries need to be realized which can be obtained in many different ways. One of them is the use of available thick- and thin-film based microfabrication technologies. Once the desired geometries are achieved, spatial averaging by the sensor occurs automatically and instantaneously, without the need for stirring or other type of homogenization.

Electrochemical transducers that make use of special sample/electrode geometries to achieve automatically that the output of the electrochemical detection scheme reflect instantaneous spatial average concentrations in the sample analyzed are provided. The approach works for both voltammetric and amperometric (output: current or its differentials), and potentiometric (output: voltage) schemes. It can give exact results for the former, and approximate results for the latter schemes. This approach is applicable to non-stirred (steady) samples that exhibit spatial inhomogeneities in chemical composition and a well-defined spatial symmetry of the said inhomogeneities (e.g. radial symmetry) or spatial degeneration of the sample/electrode layout (e.g. a nearly two-dimensional sample such as in a thin layer cell).

Where there is a reagent source or sink of a chemical connected (adjacent) to a steady sample then concentration profiles according to the induced diffusion patterns will develop inside that sample. If sample shape and the location of the source/sink are such that some symmetry arises in the induced concentration distributions inside the sample then, irrespective of time (evolution of concentration profiles in time) and whether reagent addition (source) or "subtraction" (sink) occurs, selection of the geometry (shape and location with respect to the sample as a whole) of the sensor such that its output will reflect three-dimensional (not interfacial) concentrations at all times and automatically, is possible. Designs can be made such that this output will reflect either true, or approximate, spatial average concentrations.

Such symmetric concentration profiles (inhomogeneities) can develop also due to certain initial conditions related to a samples, for example, due to how it was obtained, sampled, or made.

To achieve automatic spatial averaging, the sensor preferably has a shape and layout such that each of its segments has an area (or length for a nearly "one-dimensional" sensor) proportional to the total volume of the corresponding segment of the sample. This will produce true spatial averaging for linear sensing schemes, i.e. for voltammetry and amperometry (when output is current or its differentials), and an approximately spatial average for logarithmic schemes, i.e. for potentiometric sensing (when the output is a voltage).

EXAMPLES

1. Radial (spherical) symmetry

With reference to FIG. 9, A sample holder 10 includes a substrate or plate 12, including upper and lower surfaces 14 and 16 respectively, and a sample container or hydrophobic ring 18, affixed to the surface of the substrate 14. A sample droplet 24 of the substance to be studied is applied to area 22 of the substrate surface 14 and centered automatically by the hydrophobic ring 18 and natural surface tension and adhesion/repulsion forces. A spatially averaging sensor, or electrode 20, is disposed within the sample 24.

The substrate 12 is constructed from a material such as Pyrex® or ceramic, which is both unreactive towards the chemicals under investigation and an electrical insulator. Surface 14 is preferably flat, but may optionally be indented to hold the sample droplet.

A source or sink 26, such as a junction hole, permits ingress of chemicals to the sample or egress therefrom. FIG. 9 shows the source 26 in the center of the hemispherical sample 24. For such a configuration, the electrode 20 is preferably either a two-dimensional electrode, or a nearly one dimensional one, for example, a microfabricated thin or thick film "wire" deposited on to the substrate surface 14. The electrode is preferably constructed of platinum, but other conductive materials known in the art may also be used. The configuration of the electrode 20 is selected according to the concentration profile within the sample 24. FIGS. 9–11 show various electrode configurations, derived by mathematical analysis of the spatial symmetry of the sample and the concentration gradient within it.

The electrode 20 is electrically connected by a platinum wire 51 to a contact pad 50, through which electrical measurements are made or voltages and currents applied. Preferably, the pad 50 is connected to automated electrochemical instrumentation (not shown).

The invention, however, is not limited to microfabrication techniques or electrodes 20 deposited on the substrate 12. Alternatively, conventional macro and microelectrodes, alone or in combination with microfabricated ones, are used for studies and analyses of the sample droplets 24.

Optionally, junction hole 26 serves as a junction between the sample droplet 24 and a reference/counter electrode (not shown). Alternatively, a reference or counter electrode is connected to the sample droplet 24 by a traditional salt bridge arrangement.

The geometry of the sample 24 is strictly reproducible due to surface tension and adhesion and repulsion forces which are strong for microliter size samples in the invented arrangements.

1.1. In the following, first a nearly onedimensional ("wire"-like) electrode 20 with linear output characteristics is considered:

$$I = I(sc(l)+b)dl \tag{I}$$

where I is output (i.e. current or its differential), I is the integral from l=0 to L (the total length of the electrode) and s and b are slope (sensitivity) and background signal of the electrode, respectively; c is local concentration at sensor length l, and l is the arc length of the line outlining the sensor. Parameters s and b are both meant for unit sensor length. The preferred sensor shape is selected such that the output I is related to the spatial average concentration C in the sample in the following way:

$$I = SC + B \tag{II}$$

where S=sL and B=bL. The integral in (I) leads also directly to the latter equations and (with equation (II)) to $$Ic(l)dl = Irw(r)c(r)dr = CL \tag{III}$$

where Ir is integral in polar coordinates from R0 to R (R is no greater than the sample radius), r is the distance from the center on the base of the sample, and w(r)=dl/dr is an appropriate weighting function that transforms c(r) dr to c(l) dl. The origin of the polar coordinate system is chosen to be the center of the semispherical sample. From this equation, it is possible to find w(r) such that equation (II) and (III) will hold, which occurs when $$w(r) = dl/dr = 3Lr^2/(R^3 - R0^3) \tag{IV}$$

From this, l(r), i.e. sensor length versus radius, can be determined which implicitly contains full geometrical information about the shape of the sensor. To obtain a more convenient and explicit mathematical form, polar angle θ versus radius can be derived from equation (IV):

$$\theta + \theta_0 = 0.5 \, (\mathrm{sqrt}(a^2r^4 - 1) - \arctan \mathrm{sqrt}(a^2r^4 - 1)) \tag{V}$$

where sqrt stands for "square root" and a is a parameter to be freely chosen, and $\theta_0$ is polar angle at the sensor's closest point to the center, for which situation $ar^2 = 1$.

Figure 10A:
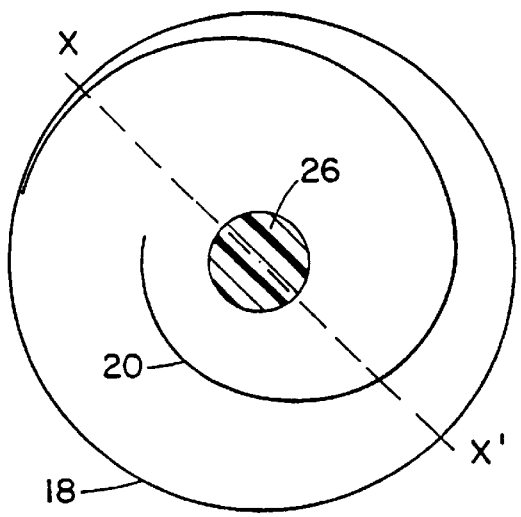
FIGS. 10(A)–10(D) are a series of top views of spatial averaging electrode geometries for use in an apparatus for electrochemical analysis of a non-homogeneous sample in accordance with the present invention.

This equation defines a special spiral shape, an example of which is shown FIG. 10A. FIG. 10 shows various top views of substrate upper surface 14 with the pattern of the deposited averaging sensor 20, and the source or sink of a chemical 26 at the center of annulus 18. Sensor 20 senses either the chemical or some property of the sample that is influenced by the chemical.

Figure 10B:
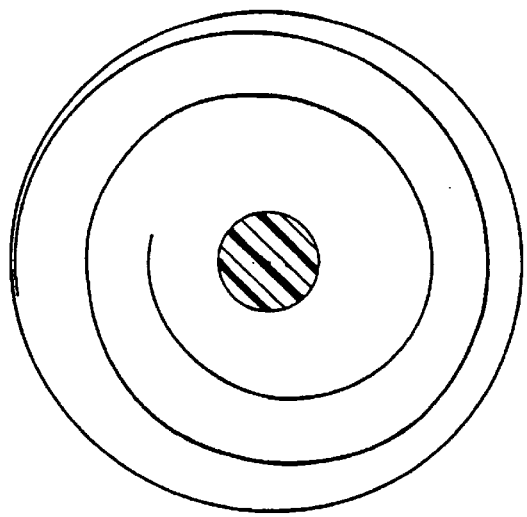

As opposed to the one turn spiral shown in FIG. 10A, FIG. 10B shows a longer, two turn spiral obtained with a larger value chosen for parameter a. "a" defines the length of the sensor 20 for a given sample radius (X–X').

Figure 10C:
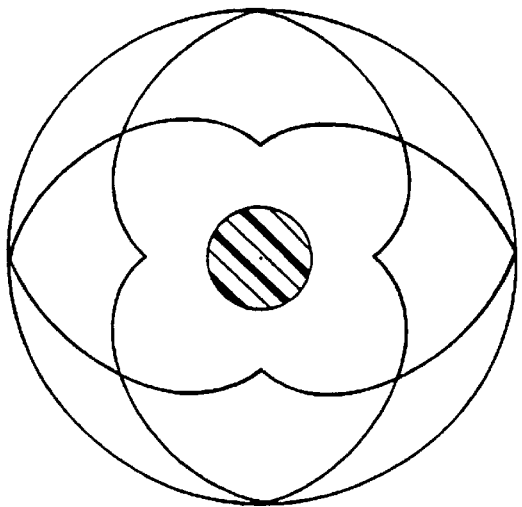
Figure 10D:
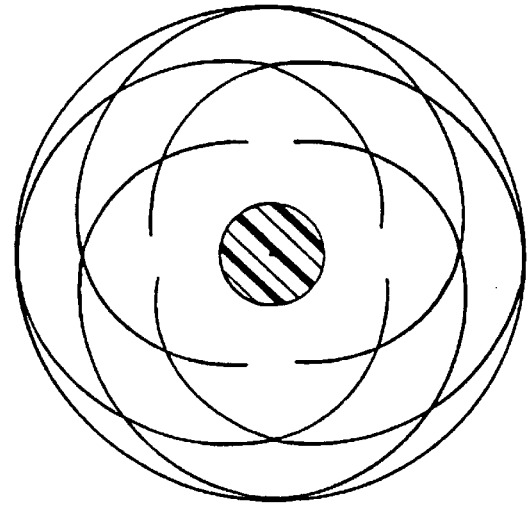

Segments of spirals calculated with equation (V) can also be rotated and reflected in different ways, and used together, such as the complex pattern of FIG. 10C, which shows an averaging sensor 20 with redundancies (more than one line in every radial direction, with 4 intercepts with each other) to give rise to a more robust sensor. This approach is useful when imperfections in sensor fabrication or wear can cause ruptures and discontinuities in the sensor made. Some deviations from the assumed ideal radial symmetry can also be compensated for with such designs. FIG. 10D shows finally an even more intricate pattern, also corresponding to equation (V).

Note that all these patterns are suitable for fabrication with state-of-the-art microfabrication procedures.

Equation (V) provides an exact solution for linear electrochemical sensors. A simpler approximate solution can be obtained for either relatively long sensors or far from the center, i.e. when $a^2r^4$ is much larger than 1:

$$\theta + \theta_0 ar^2/2 \tag{VI}$$

FIG. 11B shows an example for a sensor 20 designed based on equation (VI), as opposed to the "exact" design shown in FIG. 11A, derived from equation (V), for the same problem. The latter solution for any given a "stops" predicting a continuous line at a finite distance from the center, where equation (V) becomes imaginary. This occurs when the sensor 20 becomes radial, i.e. when dl/dr=1. Beyond this point(even closer to the center), it clearly cannot become even "shorter" per unit radial change, unless it is allowed to lose continuity (a transition from one to zero dimension) which explains the physical meaning of the (exact) solution becoming imaginary. This singularity, however, does not exist in the approximate solution of equation (VI). On the other hand, this approximation is best used at longer distances from the origin.

1.2. For a nearly one-dimensional and logarithmic sensor 20, a semispherical sample 24 and radial symmetry as discussed above leads to the same solutions (equations (V) and (VI) but with some terms neglected. The derivation, not shown here, justifies neglecting these terms only if the inhomogeneities in the sample 24 are relatively small. This is the case for very small samples (in the order of 1–20 microliter in volume) and relatively high diffusivities of the species involved in the measurements.

FIG. 9 shows an example of an actual sensor of this type, as deposited on the base of a 20 microliter sample. The platinum spiral electrode 20 senses approximately the spatial average concentration of a redox species inside the 20 microliter semispherical sample 24 if homogeneities due to the source or sink 26 present in the center are not too large. Sensing is based in this case on Nernst's equation modified for redox couples.

1.3. For a two-dimensional sensor, a suitable solution to the same radially symmetrical problem can be an electrode becoming wider at larger radii proportionally to $r^2$. The reason for this is that semi-spherical "shells" at different radii have an incremental volume, dV, proportional to $r^2$:

$$dV = 2\pi r^2 dr \quad (VII)$$

(This equation was also used in the derivation of the weighting function, w(r) above, resulting in equation (IV)). The "circular" width, cw (i.e. length of a circular line at r that is fully within the sensor) must then be:

$$cw(r) = ar^2 \quad (VIII)$$

where a is, again, an adjustable parameter defining the actual widths of the sensor. Again, several such sensors can be deposited on the same base to obtain redundancy. In this case, a may be chosen such that the individual sensors obeying equation (VIII) merge into each other at r=R, thus producing a full circle at the edge of the sample that electrically links all segments to each other and a contact pad (not shown).

The same discussion applies here to linear versus logarithmic sensors as outlined above for the one dimensional case.

2. Cylindrical Symmetry

The source or sink 26 is in the central axis of a cylindrical sample 24 or at its edges. Similar derivations can be performed for such problems as above, except that a one-dimensional sensor can then be laid out in two or three dimensions as necessary, and in the derivation of the weighting function, w(r), instead of equation (VII), $$dV = 2\pi r dr \quad (IX)$$

is to be used.

Other types of symmetries and layouts can be also handled using the principles outline above.

3. Spatial Degeneration of the Sample/Sensor Layout

For samples with non-symmetric inhomogeneities design of sensor 20 is possible, but only with reduced practicality. An example for this would be a three-dimensional matrix of dot sensors with sensing dots uniformly distributed over the entire sample 24, at a reasonable density matching the sharpest changes in inhomogeneities occurring in all samples. The dots are optionally connected with non-sensing (insulated) wires to a common contact pad.

More practical arrangements are obtained for situations with some spatial degenerations. An example is a sample 24 whose width in one dimension is very little compared to diffusion time in that direction, making the sample effectively homogeneous in that direction. Then, a uniformly distributed system of dots in the plane perpendicular to the said direction could produce a good spatial average signal. A full planar sensor in that plane (which is effectively equivalent to a thin layer cell) is also a solution to the problem. Similarly, an array of band electrodes, and many other arrangements of ultimately uniform distribution and sufficient spatial resolution in the same plane would also be effective. Similar solutions to other types of degenerations can be found based upon the same principles.

IV. Electrochemical pH-Statting

Figure 12:
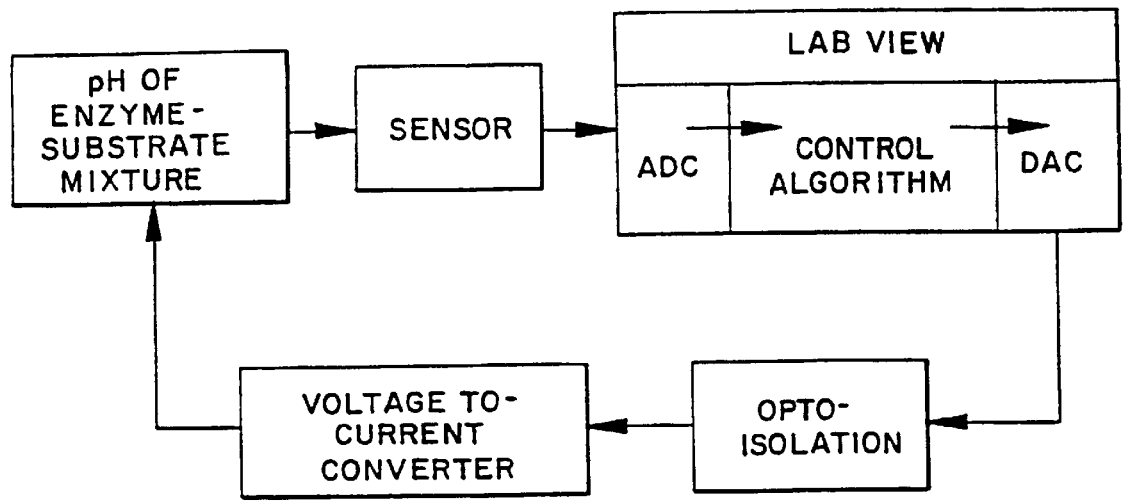
FIG. 12 is a schematic diagram of an apparatus for electrochemical pH-statting in accordance with the present invention.
Figure 13:
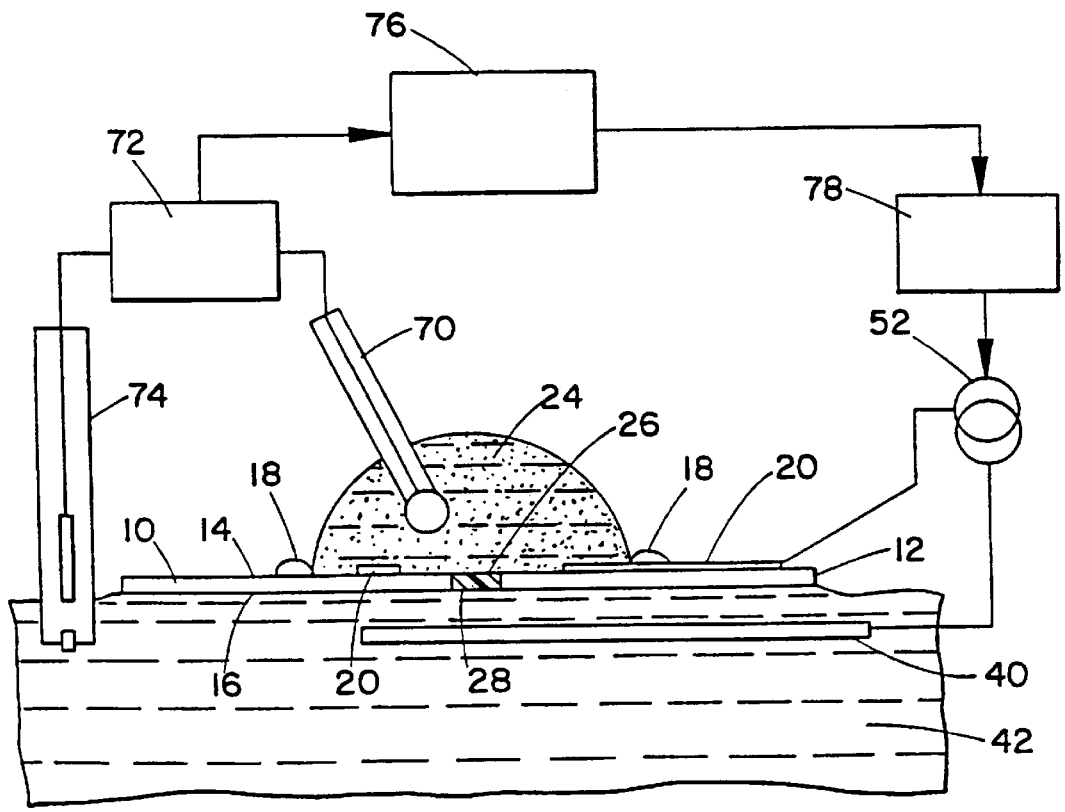
FIG. 13 is a side view of an apparatus for electrochemical pH-statting in accordance with the present invention.

With reference to FIGS. 12 and 13, an apparatus for electrochemical pH-statting includes many of the components heretofore described. Like components are numbered accordingly. A sample holder 10 includes a substrate or plate 12, including upper and lower surfaces 14 and 16 respectively, and a sample container or hydrophobic ring 18, affixed to the surface of the substrate 14. A working electrode 20, is preferably connected to the surface 14 of the substrate, centered within an area 22, bounded by the hydrophobic ring 18. A sample droplet 24 of the substance to be studied is applied to area 22 of the substrate surface 14 and centered automatically by the hydrophobic ring 18 and natural surface tension and adhesion/repulsion forces. Optionally, a jet system (not shown) directs a flow of gas tangentially at the sample droplet 24.

The substrate 12 is constructed from a material such as Pyrex®, which is both unreactive towards the chemicals under investigation and an electrical insulator. Surface 14 is preferably flat, but may optionally be indented to hold the sample droplet. The thickness of the substrate 12 is preferably of the order of 0.25 mm.

The electrode 20 shown in FIG. 13 is preferably a gold or platinum working electrode. For sample droplets of 20 $\mu$L volume, the electrode is optionally microfabricated by thin-film sputtering a ring of approximate dimensions 2.2 mm diameter, 0.2 mm width, and 5000 Å thickness onto the area 22 of the surface of the substrate 14.

The electrode is electrically connected to a contact pad 50, through which electrical measurements are made or voltages and currents applied. Preferably, the pad 50 is connected to automated electrochemical instrumentation 52.

The working electrode 20 generates hydrogen or hydroxyl ions in the sample 24 by applying a current to the sample. For hydrogen ions the electrode 20 is anodic, for hydroxyl ions, cathodic.

The invention, however, is not limited to microfabrication techniques or electrodes 20 deposited on the substrate 12. Alternatively, conventional macroand microelectrodes, alone or together with microfabricated ones, are used for studies and analyses of the sample droplets 24.

A pH electrode 70 is inserted into the sample 24. A pH meter 72 and a reference electrode 74, such as a SCE, are attached to the pH electrode.

Optionally, a counter electrode 40 immersed in an electrolyte solution 42 is in electrical contact with the sample 24.

A stainless steel counter electrode 40 in a 0.1 M KNO3 electrolyte 42 provides a good counter electrode. Optionally, the electrode 40 is connected to electrochemical instrumentation 52.

Junction hole 26 preferably serves as a junction between the sample droplet 24 and the counter electrode 40 and electrolyte 42. Alternatively, the reference or counter electrode 40 is connected to the sample droplet 24 by a traditional salt bridge arrangement.

The geometry of the sample 24 is strictly reproducible due to surface tension and adhesion and repulsion forces which are strong for microliter size samples in the invented arrangements.

Optionally, reagents are added to the sample droplet 24 by controlled diffusion through gel, or salt bridge 28. Extremely low delivery rates are achievable in this way. In addition, the beginning of delivery can be timed at any point in the analysis. When required, the diffusive delivery rate of the reagent is enhanced by placing the junction hole 26 off center, to make use of the higher flow rates there.

The invention provides ways to design devices and method to perform pH-statting in macroscopic, intermediate and microscopic size samples without the need for mechanical (convective) reagent addition, by using electrochemical hydrogen or hydroxyl ion generation to compensate for spontaneous pH shifts in samples. In the intermediate range (a few microliters in volume) further special arrangements are part of the invention. Enzyme activities and other parameters can be determined with this invention in cost effective ways in closed samples.

The method avoids using moving mechanical parts by performing reagent addition by electrochemical means, for the same (and similar other) applications as listed above. This means that adding a base is done, instead of convective addition of a base solution, by injecting current via an inert, negatively poised electrode so that water in the sample is split generating hydroxyl ions (accompanied by generating bubbles of hydrogen at the injecting electrode). Similarly, acid can be added by a positively poised electrode splitting water into hydrogen ions and bubbles of oxygen. The counter electrode needed is separated from the sample by an electrochemical junction so that the reaction products (mainly hydrogen ions in the base generation, and hydroxyl ions for acid generation in the sample) do not disturb the pH in the sample. It is also necessary to make sure that virtually all current injected is "used" for generating the desired species and not some other reaction products. The result of a determination is then the value of the actual steady state current (divided by Faraday's constant, since one electron passed is equivalent to the generation of one hydrogen ion at the positive electrode and one hydroxyl ion at the negative electrode) that is necessary and sufficient to counteract the chemical or biochemical reactions occurring in the sample at steady state. The samples used are closed systems, i.e. all pH changes are due only to processes in the sample and current injection by the instrument.

Advantages of this approach are numerous. It does not require reagents (it is reagentless) and thus, there is no need for reagent reservoirs). There is no need for any moving mechanical parts. Regulation and feedback control of current in a feedback loop is straightforward and easy. There is virtually no lower limit for the value of current that can be injected. This opens up the above-listed applications to small (microliter) and even microscopic samples, if needed. The instrument can be made compact (consisting of very few parts), small, portable, and (especially, its most used elements like the ones exposed to subsequent samples) even disposable if needed. The variable reflecting the actual result of the determination is the injected steady state current itself (corrected for by using Faraday's constant) and this current is automatically known if a calibrated current generator is used for its addition, i.e. no "measurement" other than that of pH is needed. Existing microfabrication technologies can be used to fabricate the device's main elements especially in the microliter sample volume range, rendering serial production extremely cost effective.

In the literature, this approach cannot be found as applied for enzyme activity determinations and the other above-listed applications. Feasibility of electrochemical pH-statting, however, has been proved in our preliminary studies.

The literature includes mainly electrochemical "buffering" of the enzyme layer in enzyme based sensors to the optimum pH for the enzyme employed irrespective of the pH and buffer capacity of the samples. However, this type of application has nothing in common with the aims of this invention since the goal in the cited references is not pH-statting of a sample but only (approximate) pH-statting of a part of a small device immersed into the sample. The objective of such schemes is to measure some steady substrate concentration in the samples, such as e.g. glucose, and not to learn anything about the enzyme employed to perform the measurement. Also, the sample size is immaterial. The total enzyme amount and/or activity inside the sensor is of no interest either. In fact, no care is taken for the quantitative use of current: it does not matter how much current is used to achieve relatively constant pH in the sensor's enzyme layer. Because of diffusive chemical exchange between the sample and the sensor's enzyme layer, and the finite buffering capacity of the sample, the current injected could not even be used to obtain such information since pH in the samples is variable and typically, different from the set pH inside the sensor.

Other types of applications (e.g. *J.Membr.Biol.*, Malnic G., Lopes A., Cassola A., Berardi A. et al., 118, pg. 121, ©1990) determines hydrogen ion fluxes in vivo, in live biological preparations (tissues, renal tubules, etc.) by stabilizing the pH electrochemically. Here, the "sample" has no boundaries, or in other words, it is not a closed system: the sources of the ions whose flux is measured are in many unspecified locations, away from where the sensing device is set up and their flux at one point (or in a small area) in the system is measured.

Some other applications of electrochemical hydrogen or hydroxyl ion generation in the literature aim to perform acid/base titration using currents injected into steady or flowing samples (Luo et al., Nagy et al.). In such cases, however, there is clearly no pH-statting involved at all.

On the other hand, in the applications envisioned in this invention, the entire (total) current injected is of crucial importance since it is that counts when the final value for enzyme activity for a particular sample is obtained. The same is the situation when the scheme is used for determining other parameters (neutralization capacity of a drug, etc., as listed earlier). The amount of the entire sample which is finite and has clear non-permeable boundaries is quantitatively pH-statted, and no effects external to the sample contribute to pH changes inside the sample: all pH changes to be compensated for originates from processes occurring within the sample during the determination. All these criteria make the aims of this invention clearly distinct from any other schemes published in the literature involving some use of electrochemical generation of hydrogen or hydroxyl ions.

The invention provides simple, cost effective, reproducible and, if needed, even disposable arrangements for pH-statting by electrochemical reagent generation in samples of a broad range of volumes, from the usual milliliter to the lower microliter range and beyond, down to microscopic samples. Hydrogen or hydroxyl ions, as needed, are generated by injecting current into the sample by a working electrode, i.e. an anode or cathode, respectively. The counter electrode at which the complementary ion is generated is separated from the sample by an electrochemical junction so that sample pH is only influenced by the chemical and/or biochemical processes occurring in it and the ions generated at the working electrode. During pH-statting, sample pH is monitored by a pH electrode or other suitable sensing schemes (e.g. pH-sensitive optical absorbance or fluorescence). The actual pH thus measured is either frequently or continuously compared to the set (desired) pH and a feedback control system adjusts the current (value and direction) actually injected such that the ions generated at the working electrode will compensate for the observed spontaneous changes in pH. The injected current value can be at, or near, the required level. Thus, for pH-statting to converge to a constant (set) pH may require a short time or in some cases longer times. Convergence may happen asymptotically or with some swings (instabilities). The samples in the invention are finite and closed systems, apart from the electrochemical junction whose action as a source or sink of chemicals must be negligible. This approach is meant to be used for enzyme activity determinations, neutralization measurements, assessing dissolution rates, acidity/alkalinity, and biological acid/base production and similar other schemes in closed systems (i.e. sample boundaries impermeable to the species in question are required except for the interface with the working electrode and the junction) The result of an actual determination is the steady state current whose injection produces the desired set pH value in the sample divided by Faraday's number, to yield the molar amount of injected ions per unit time. Therefore, it is necessary to ensure that all or nearly all current injected produce only the desired type of ion (hydrogen or hydroxyl) at the working electrode which can be achieved by relatively high current densities (i.e. small electrodes). No such requirement is to be fulfilled for the counter electrode. While the invention is relevant to both macro and microscopic samples, the range of sample volumes where this invention has further unique aspects is in the low microliter range. Such samples can be kept on a hydrophilic substrate without the need for any vessel, spatially confined into a well-defined and reproducible shape only by surface tension and capillary forces. The working electrode and eventually also the pH sensing element can be microfabricated on top of the substrate. This arrangement joins another compartment via a junction, containing a buffer solution and an immersed counter electrode. The sample holding substrate (with or without the deposited electrodes/sensors) can be made disposable, if needed.

EXAMPLES

The need for pH-statting in ordinary size samples (milliliters) is obvious. Sample volumes in the microliter range have not been covered thus far by existing pH-statting technologies. Their importance lies mainly in the fact that body fluids are not available in some cases in larger quantities (e.g. premature babies, neonatal care, etc.). Precious materials (like most enzymes) or products and intermediates in research and industry are also worth saving since they typically cannot be reused after analysis. Microscopic samples are encountered typically in research.

In the following, devices and methods according to this invention will be described in sections dedicated separately to each of the above sample volume ranges.

(1) For macroscopic samples in the low milliliter range, many different setups are possible within the framework of this invention. One possibility is to place the sample solution into a small beaker which is connected to another one through an agar gel junction. The junction should be as short (thin) as possible to avoid a significant ohmic voltage drop to develop along its axis due to the currents passing through it during pH-statting. Cross-sectional area of the junction is determined as a trade-off between minimizing ohmic drop (which requires the largest possible cross-section) and minimizing diffusional chemical exchange between sample and the buffer solution in the other side (which requires a minimal cross-section). An inert working electrode (e.g. made of Pt or Au) is inserted into the sample, and a similar counter electrode into the buffer solution in the other beaker. The two are electrically connected by ionic conductors which are the sample, the junction and the buffer solution and hooked up to a current generator whose output is feedback controlled by a PID or other controller. Sample pH is monitored with a pH glass electrode immersed into it. If it is not a combination electrode, then the reference electrode can be also placed inside the sample. It can also be immersed into the buffer solution in the other beaker if the ohmic drop through the junction and the solution compartments is negligible. If this is not negligible then the pH sensor's output can be corrected for it, by using the actual current values and the overall ionic resistance between pH sensor and its reference.

Such an arrangement (not shown) produced valid enzyme activity results in stirred samples of cholinesterase of physiological concentrations a few milliliters in volume. The system achieved pH-statting automatically and within about a minute after starting the control (not shown), using a simply fuzzy-logic computer algorithm for feedback control. The pH of the buffer used by adjusted to the set pH (7.4 which is optimal for cholinesterase in physiological samples) so that during successful pH-statting no diffusive addition of hydrogen or hydroxyl ions to the sample during successful pH-statting no diffusive addition of hydrogen or hydroxyl ions to the sample could occur from/via the junction.

(2) In microscopic samples, evidently, microelectrodes are needed. The breaker containing the buffer and counter electrode in the previous example can be replaced with a pulled capillary with an agar or polyacrylamide junction in its microscopic tip. The capillary is then filled with a buffer solution into which a counter electrode is inserted from the back end of the pipet. This arrangement plus a working microelectrode are inserted then into the microscopic sample, e.g. under a microscope. Sample pH can be monitored using a suitable pH dye dissolved or diffusionally delivered into the sample. All special precautions described above apply here, too (e.g. the ones about ohmic drop or buffer pH).

(3) In the intermediate volume range, i.e. in microliter samples (e.g. 1–20 microliter), special arrangements that are also unique to this invention can be incorporated into the instrument and methods design, beyond those aspects of the above descriptions that are applicable also here. One possible arrangement (FIG. 11) shows the block diagram of a realized system (FIG. 11). The side view of the "wet chemistry" part of the system (FIG. 12) displays a 20 microliter enzyme sample (whose activity needs to be determined) as a semispherical drop on top of a solid holder (Pyrex® plate), confined into a semi-sphere and centered by a circular hydrophobic ring deposited onto the holder (not shown) which has the right internal diameter to enforce the shape of an exact semisphere on the sample. A gold working electrode is deposited by microfabrication technologies onto the Pyrex® in the form of a ring with connection to a contact pad outside the sample. SCE is the reference electrode necessary for the micro pH electrode inserted into the sample. The sample drop is homogenized by rapidly rotating it with a mild gas jet directed tangentially at it (not shown). Optical isolation is needed to avoid electrical crosstalk between the pH measurement and the current injecting circuit. LabView is a computer is used to handle the measurement of pH and use it for feedback control.

Even smaller samples can be handled with a similar arrangement but the gas jet rotation system (or any other type of stirring) can be omitted since spontaneous diffusive homogenization inside samples in the order of 1–2 microliter in volume is efficient enough (especially that hydrogen and hydroxyl ions are the fastest existing chemical species to diffuse).

What is claimed is:

1. An apparatus for performing measurements on a small liquid sample including:
    a substrate, including an upper surface for supporting the sample to be investigated, and a lower surface;
    a container, sealed to the upper surface of the substrate for containing the sample on the substrate;
        the container including an annulus that confines the sample on an area of the substrate upper surface bounded by the annulus;
    a junction hole, passing through the substrate and connecting the upper surface of the substrate with a lower surface of the substrate,
    a membrane covering the junction hole, the membrane permitting diffusive movement of a reagent through the junction hole and into the sample;
    a source of reagent, disposed adjacent to the lower surface of the substrate for supplying reagent to the membrane; and,
    a detector for detecting a measurable change in a property of the sample.

2. The apparatus of claim 1, wherein:
    the detector includes optical measuring equipment, the optical measuring equipment including a light source for directing light toward the sample and a receiver for receiving light from the sample.

3. The apparatus of claims 2, wherein:
    the source of reagent includes a window, the window located such that light from the light source passes through the window and through both the reagent and the substrate to the sample.

4. The apparatus of claim 2, wherein:
    the substrate includes a reflective coating, the coating reflecting light from the light source into the sample.

5. The apparatus of claim 1 further including:
    a mixing system for mixing the sample;
    the mixing system including a source of gas for directing a controlled flow of gas at the sample, the flow of gas rotating and mixing the sample as desired.

6. The apparatus of claim 1 wherein:
    the membrane includes a voltage sensitive gel for controlling the rate of reagent diffusion through the membrane by applying a voltage across the gel.

7. An apparatus for performing hydrodynamic electrochemical studies and analyses on a small liquid sample including:
    a substrate including, an upper surface for supporting the sample to be investigated;
    an electrode, electrically connected to the sample;
    a container, sealed to the upper surface of the substrate for containing the sample on the substrate,
        the container including an annulus which confines the sample on an area of the substrate upper surface bounded by the annulus;
    a source of gas, for directing a flow of gas toward the sample, thereby causing controlled liquid flow over the electrode.

8. The apparatus of claim 7, wherein:
    the electrode includes a gold ring working electrode, centered on the area of the upper surface of the substrate bounded by the annulus.

9. The apparatus of claim 7 including:
    a junction hole, passing through the substrate and connecting the upper surface of the substrate with a lower surface of the substrate;
    a gel disposed in the junction hole;
    a second electrode being disposed in an electrolyte, the electrolyte contacting the gel at the lower surface of the substrate such that the electrode is in electrical contact with the sample.

10. The apparatus of claim 7, including:
    a reagent in solution, the solution contacting the gel at the lower surface of the substrate, such that the reagent diffuses through the gel and into the sample.

11. A method for performing measurements on a small liquid sample, the method comprising:
    disposing a sample to be tested in the apparatus of claim 1 by depositing the sample on the upper surface of the substrate, in the area bounded by the annulus;
    adding a reagent to the droplet by diffusion of the reagent through the membrane;
    making measurements on the sample, the measurements corresponding to a property of the sample.

12. A method for performing hydrodynamic electrochemical studies and analyses on a small liquid sample, the method comprising:
    disposing a sample to be tested in the apparatus of claim 7 by depositing the sample on the upper surface of the substrate, in the area bounded by the annulus;
    directing a flow of gas onto the sample, thereby causing controlled liquid flow over the electrode;
    conducting electrochemical studies on the sample.

13. An apparatus for electrochemical analysis of a non-homogeneous sample including:
    an electrode, disposed in a solution of the sample to be analyzed;
    the shape of the electrode and the disposition of the electrode within the sample being selected such that an output of the electrode relates to the spatial average of a property of the sample.

14. The apparatus of claim 13 wherein:

the property of the sample is the chemical composition of the sample.

15. An apparatus for electrochemical pH-statting of a sample including:

a working electrode disposed in the sample;

a counter electrode;

the working electrode applying a current to the sample to generate in the sample one of the group of ions comprising hydrogen and hydroxyl ions;

the counter electrode being separated from the sample by an electrochemical junction, the counter electrode generating a complementary ion that is separated from the sample by the electrochemical junction so that the pH of the sample is not influenced by the complementary ion;

a pH detector disposed in the sample which detects the pH of the sample; and, a controller which regulates the current applied by the working electrode to achieve a preselected pH int he sample.

16. The method of claim 11 wherein the property of the sample is the chemical composition of the sample.

* * * * *